United States Patent
Kato

(10) Patent No.: US 10,864,360 B2
(45) Date of Patent: Dec. 15, 2020

(54) MICRONEEDLE UNIT

(71) Applicant: TOPPAN PRINTING CO., LTD., Taito-ku (JP)

(72) Inventor: Hiroyuki Kato, Taito-ku (JP)

(73) Assignee: TOPPAN PRINTING CO., LTD., Taito-ku (JP)

(*) Notice: Subject to any disclaimer, the term of this patent is extended or adjusted under 35 U.S.C. 154(b) by 446 days.

(21) Appl. No.: 14/992,560

(22) Filed: Jan. 11, 2016

(65) Prior Publication Data

US 2016/0121092 A1 May 5, 2016

Related U.S. Application Data

(63) Continuation of application No. PCT/JP2014/067185, filed on Jun. 27, 2014.

(30) Foreign Application Priority Data

Jul. 11, 2013 (JP) ................................. 2013-145569

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01); *A61M 2037/0053* (2013.01)

(58) Field of Classification Search
CPC ...... A61M 37/0015; A61M 2037/0023; A61M 2037/0046; A61M 2037/0053;
(Continued)

(56) References Cited

U.S. PATENT DOCUMENTS 6,945,952 B2 * 9/2005 Kwon ................. A61B 17/205
  604/46
7,842,008 B2 * 11/2010 Clarke .................... A61M 5/46
  604/117
(Continued)

FOREIGN PATENT DOCUMENTS

JP  2010-029634 A  2/2010
JP  2010-516337 A  5/2010
(Continued)

OTHER PUBLICATIONS

International Search Report dated Jul. 29, 2014 in PCT/JP2014/067185, filed Jun. 27, 2014.

*Primary Examiner* — Bhisma Mehta
*Assistant Examiner* — William R Frehe
(74) *Attorney, Agent, or Firm* — Oblon, McClelland, Maier & Neustadt, L.L.P.

(57) ABSTRACT

A microneedle unit includes a liquid holder, a microneedle, and a support member. The liquid holder has an enclosure that holds liquid including a substance to be administered. The microneedle has a base body and protrusions extending from the surface of the base body. The protrusions are of a hardness sufficient to pierce the liquid holder. The support member supports the base body in a state such that the microneedle is arranged at a position in which the tips of the protrusions and the enclosure holding the liquid are opposed to each other with a gap provided therebetween. The tips of the protrusions can be displaced to a position where the tips of the protrusions penetrate through the liquid holder in response to an external force applied to the base body.

20 Claims, 3 Drawing Sheets

(58) Field of Classification Search
CPC .. A61M 2037/003; A61M 2037/00385; A61M 2037/0061; A61M 37/0076; A61M 37/0084; B81C 1/00111; B81B 2201/055
See application file for complete search history.

(56) References Cited

U.S. PATENT DOCUMENTS

| | | | |
|---|---|---|---|
| 2008/0183144 A1 | 7/2008 | Trautman et al. | |
| 2008/0200883 A1 | 8/2008 | Tomono | |
| 2008/0208134 A1 | 8/2008 | Tomono | |
| 2009/0099427 A1* | 4/2009 | Jina | A61B 17/205 600/309 |
| 2009/0131964 A1* | 5/2009 | Freeman | A61B 5/1427 606/181 |
| 2009/0198189 A1* | 8/2009 | Simons | A61M 37/0015 604/173 |
| 2009/0292254 A1 | 11/2009 | Tomono | |
| 2009/0292255 A1 | 11/2009 | Tomono | |
| 2010/0100005 A1* | 4/2010 | Mir | A61B 5/685 600/556 |
| 2010/0168715 A1* | 7/2010 | Cassemeyer | A61M 37/0015 604/520 |
| 2010/0179473 A1* | 7/2010 | Genosar | A61M 5/14248 604/70 |
| 2011/0251561 A1* | 10/2011 | Inou | A61M 37/0015 604/173 |
| 2012/0184916 A1* | 7/2012 | Kobayashi | A61M 37/0015 604/180 |
| 2012/0265145 A1 | 10/2012 | Mefti et al. | |

FOREIGN PATENT DOCUMENTS

| | | | | |
|---|---|---|---|---|
| JP | 2011-055860 A | 3/2011 | | |
| JP | 2013-515524 A | 5/2013 | | |
| WO | WO 2007/007128 A1 | 1/2007 | | |
| WO | WO-2007007128 A1 * | 1/2007 | | A61B 17/205 |
| WO | WO 2008/007906 A1 | 1/2008 | | |
| WO | WO 2008007906 A1 * | 1/2008 | | A61M 37/0015 |
| WO | WO 2008/020632 A1 | 2/2008 | | |
| WO | WO-2011027586 A1 * | 3/2011 | | A61M 37/0015 |

\* cited by examiner

MICRONEEDLE UNIT

CROSS-REFERENCE TO RELATED APPLICATIONS

The present application is a continuation of International Application No. PCT/JP2014/067185, filed Jun. 27, 2014, which is based upon and claims the benefits of priority to Japanese Application No. 2013-145569, filed Jul. 11, 2013. The entire contents of these applications are incorporated herein by reference.

BACKGROUND OF THE INVENTION

Field of the Invention

The presently disclosed technique relates to a microneedle unit provided with a microneedle.

Discussion of the Background

As a method of administering a drug into a body, a method employing a microneedle is known. As described in the patent reference 1, for example, the microneedle has a plurality of protrusions each shaped into a needle, and a base body supporting the anchors of the plurality of protrusions. In an administration method employing the microneedle, the protrusions of the microneedle are pierced in a skin tissue of the body so that perforations are formed on the skin tissue, for example. Then a liquid drug is applied on the skin tissue where the perforations are formed and the drug enters the perforations, which in turn are absorbed into the body.
Patent reference 1: WO 2008/020632

SUMMARY OF THE INVENTION

According to one aspect of the present invention, a microneedle unit includes a liquid holder having a portion for holding a liquid including a substance to be administered, a microneedle having a base body and a protrusion extending from a surface of the base body, the protrusion having a hardness that allows the protrusion to penetrate through the liquid holder, and a supporting member that supports the base body such that the microneedle is placed at a position where a tip portion of the protrusion and the portion holding the liquid are opposed to each other with a gap therebetween, and that the tip portion is movable to a position where the tip portion penetrates through the liquid holder, in response to an external force applied to the base body.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
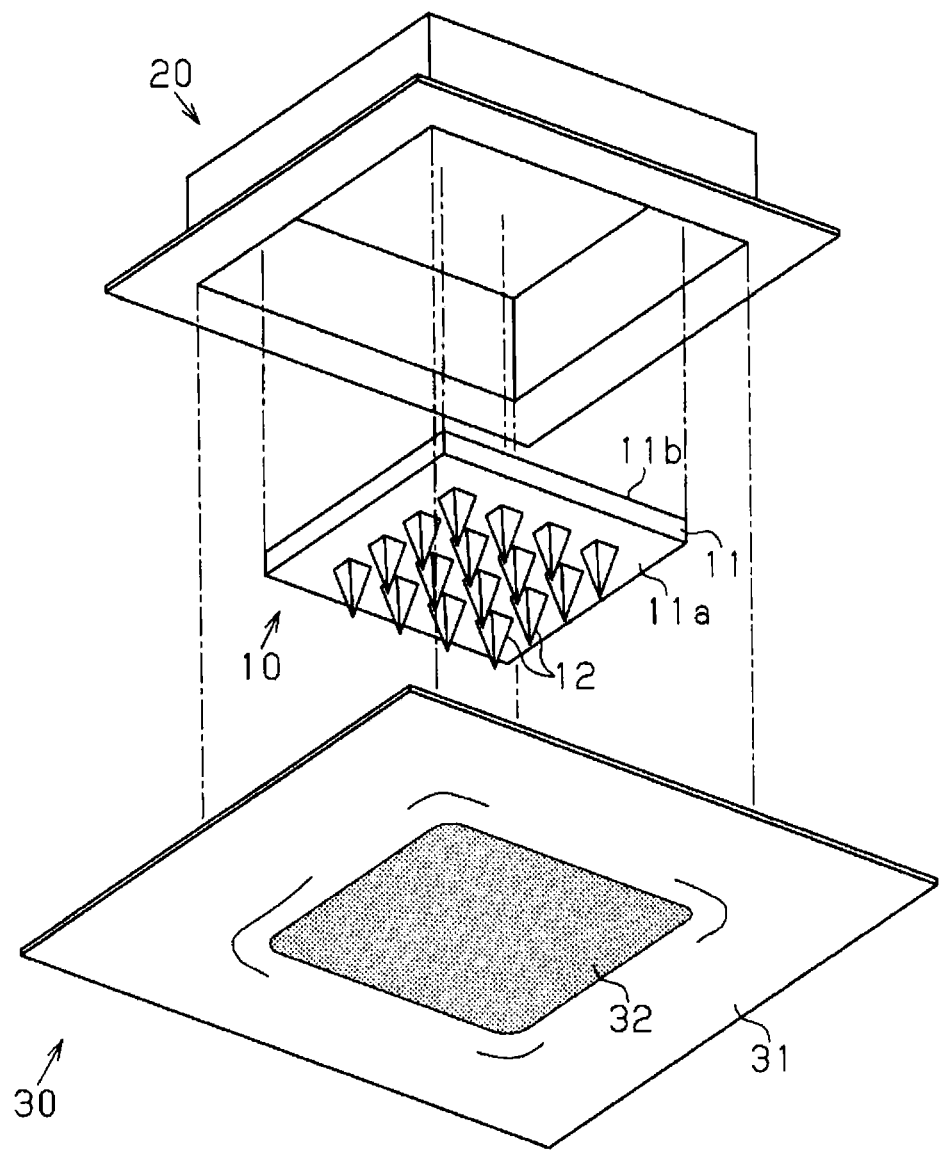
FIG. 1 is an exploded perspective view showing each element configuring a microneedle unit according to an embodiment of the presently disclosed technique.

The embodiments will now be described with reference to the accompanying drawings, wherein like reference numerals designate corresponding or identical elements throughout the various drawings.

Figure 2:
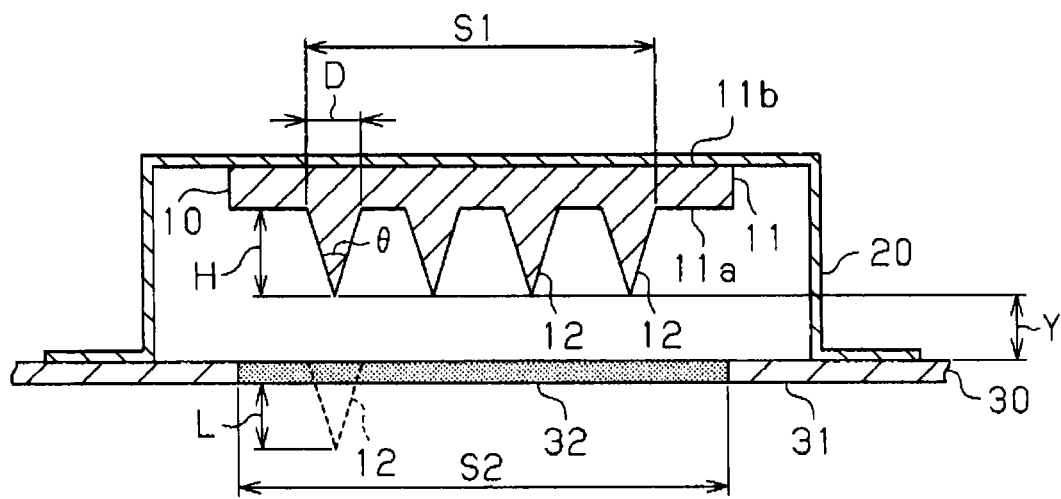
FIG. 2 is a cross sectional view showing a cross sectional structure of the microneedle unit shown in FIG. 1.

The first embodiment of a microneedle unit in the present disclosure will now be described with reference to FIG. 1 through to FIG. 5. The overall configuration of the microneedle unit is first described below. FIG. 1 is an exploded perspective view showing the microneedle unit in a dissembled manner and FIG. 2 is a cross sectional view showing a sectional structure obtained when the microneedle unit is assembled.

As shown in FIG. 1, the microneedle unit includes a microneedle 10, a supporting-member 20 supporting the microneedle 10, and a liquid holder 30 holding a liquid that contains a substance to be administered. The supporting member 20 and the liquid holder 30 configure a single closed space, and the microneedle 10 is accommodated in a space sectioned by the supporting member 20 and the liquid holder 30.

The microneedle 10 includes a base body 11, and protrusions 12 provided on the base body 11. The base body 11 has a protrusion-formed face 11a which serves as a surface of the base body 11, and a fixed face 11b which serves as a reverse-side of the base body 11. The protrusion 12 protrudes from the protrusion-formed face 11a, and the bottom sides of the protrusion 12 is joined to the protrusion-formed face 11a. In addition the protrusion-formed face 11a supports the base body of the protrusion 12.

The shape of the base body 11 can be a flat plate shape, a flexible plate shape, or a rectangular parallel-piped formation. The shape of each of the protrusions 12 can be a pyramidal shape or a conical shape. In addition, the shape of each of the protrusions 12 can be a shape wherein the tip of the protrusion 12 is not pointed, like a cylindrical or prismatic-columnar shape. Alternatively, each of the protrusions 12 can be formed by mutually combining two or more solids, such as a shape where a circular core is laminated on a cylinder. In other words, it is sufficient that each of the protrusions 12 have a shape which is able to pierce the skin tissue. The number of protrusions 12 is one or more, i.e., any number of protrusions can be provided.

The plural of protrusions 12 can be arranged regularly, or can be arranged irregularly on the surface of the base body 11. The plural of protrusions 12 can be positioned one-sided in several places on the protrusion-formed face 11a. The plural of protrusions 12, can also be arranged as a lattice form or a concentric circular form, for example.

The supporting part 20 is a concave-shaped container with an inner space. The supporting member 20 has a one side having an opening. In FIG. 1 the opening of the supporting member is positioned lower than the bottom of the supporting member 20. The microneedle 10 is accommodated in inner space of the supporting member 20, where the tip of the protrusion 12 is faced towards the opening of the supporting member 20. The depth of the supporting member 20 is formed larger than the thickness of the microneedle 10 in the extending direction of the protrusion 12.

The liquid holder 30, which is an example of a packing body, includes an enclosure 32 provided as an example of a part holding a liquid. A liquid containing a drug, which is an example of a substance to be administered, is held inside the enclosure 32. The enclosure 32 is a space surrounded by a base material 31 such as a film. The liquid holder 30 is positioned so that the enclosure 32 faces the tips of the protrusions 12. In a direction parallel with the base body 11 of the microneedle 10, the enclosure 32 has a size larger than a range in which the protrusions 12 are formed on the protrusion-formed face 11a of the base body 11.

As shown if FIG. 2, at the supporting member 20, the opening of the supporting member 20 and bottom of the supporting member 20 face each other. The fixed face 11b of the base body 11 is fixed to the bottom of the supporting member 20, and the opening of the supporting member 20 is closed with the liquid holder 30.
When there is no external force applied to the bottom of the supporting member 20, the supporting member 20 supports the microneedle 10 at a position which makes it possible such that the tips of the protrusions 12 of the microneedle 10 and the enclosure 32 of the liquid holder 30 face to each other. Between the tips of the protrusion 12 and the enclosure 32, there is a formed gap.

When the microneedle is used, the opening of the support member 20 is placed on the skin tissue through the liquid holder 30. Thereafter, the bottom of the supporting member 20 is pressed from the outside of the supporting member 20 in a direction towards the opening of the supporting member 20, and the fixed face 11b of the body base 11 is thus pressed in a direction towards the liquid holder 30. As a result, the protrusions 12 of the microneedle 10 pierces through the enclosed part 32 of the liquid holder 30 to pierce into the skin tissue. If the respective protrusions 12 have a square pyramidal shape, the bottom of each of the protrusions 12 show a square contour. Herein, FIG. 2 shows a cross section obtained by cutting the microneedle unit along the diagonal line of the bottom of the protrusions 12.

Next, each of the elements configuring the microneedle unit is described in detail.

Each of the protrusions 12 is formed in a shape that enables each protrusion to penetrate through the liquid holder 30, and has a hardness that enables each protrusion 12 to penetrate through the liquid holder 30 in a direction along where the protrusions 12 extend. The respective protrusions 12 have a height H which is defined as a length from the protrusion-formed face 11a of the base body 11 to the tip of the protrusions 12. It is sufficient that the height H of the protrusions 12 is set such that the length of the microneedle in the extending direction of the protrusions 12 is smaller than or equal to the depth of the supporting member 20 and the protrusions 12 are able to pierce the skin tissue through the enclosure 32 when the base body 11 is pressed.

Specifically, it is preferred that a length of the respective protrusions 12 which protrude from the enclosure 32 when the base body 11 is pressed, which length is defined as a maximum protruding length L, is equal to or higher than 10 µm and equal to or lower than 1000 µm. In this case where the object of perforation is human skin and the bottom of the formed perforation is set inside the corneum layer, the maximum protrusion length L is desirably higher than or equal to 10 µm and lower than or equal to 300 µm, and more preferably higher than or equal to 30 µm and lower than or equal to 200 µm. If the bottom of the perforation passes the corneum layer, and is set at a depth that does not reach the nerve layers, the maximum protrusion length is higher than or equal to 200 µm and lower than or equal to 700 µm, and more preferably higher than or equal to 200 µm and lower than or equal to 500 µm, and more preferably higher than or equal to 200 µm and lower than or equal to 300 µm. If the depth of the perforation is set to reach the dermis, the maximum of protrusion length L is preferably higher than or equal to 200 µm and lower than or equal to 300 µm.

The maximum protrusion length L of the protrusion 12, approximately equal to a value obtained by subtracting the thickness of the enclosure 32 from the height H of the respective protrusions 12. The height H of the protrusion 12 is formed to be greater than in a case where the microneedle 10 is directly pierced through the skin tissue, without going through the enclosed part 32.

The respective protrusions 12 have a width D which is the maximum length of each of the protrusions 12 in a parallel direction with the protrusion formed-face 11a of the base body 11. The width D of each of the protrusions 12 is desirably higher than or equal to 1 µm and lower than or equal to 300 µm. That is, if the protrusions 12 are a square pyramidal shape or square prism shape, for example, the contour of the bottom of each of the protrusions 12 is drawn as a square in the protrusion-formed face 11a. The diagonal line of the drawn square of the bottom of each protrusion 12 has a length which corresponds to the width D of each protrusion 12. Alternatively, if each of the protrusions 12 is a conical shape or a column shape, the diameter of the circle drawn by the bottom of the protrusions 12 becomes the width of the respective protrusion 12.

It is preferred that an aspect ratio A (A=H/D), which is a ratio of the width D of the protrusion 12 and the height H of the protrusions 12, is more than or equal to 1 and less than or equal to 10. If the tip of each of the protrusions 12 is formed in a pointed shape, and a perforation is formed to reach the dermis, it is preferred that the tip of each of the protrusions 12 has a apex angle θ of more or equal to than 5 degrees and less than or equal to 30 degrees. More preferably, the apex angle θ is more than or equal to 10 degrees and less than or equal to 20 degrees. The apex angle θ of the tip is defined a maximum value of the angle formed by the tip of the protrusions 12, in a section orthogonal to the protrusion forming face 11a of the protrusions 12. For example, if each of the protrusions 12 has a square pyramidal shape, the apex angle θ of the protrusion 12 is provided as the apex angle of an isosceles triangle whose base is a diagonal line of a square drawn by the bottom of each of the protrusions 12 and whose vertex is provided as the vertex of a square pyramid thereof.

The width D of each of the protrusion 12, the aspect ratio A and the apex angle θ are determined according to the capacity of a, of a necessary perforation or other factors. If the height H, the width D, and the aspect ratio A, and the apex angle θ are within the ranges of the above described, the formed shapes of the protrusion 12 are appropriate for forming perforations on the skin tissue.

According to the microneedle unit in the present disclosure, the distance Y between the tip of the protrusions 12 of the microneedle 10, and the enclosure 32 of the liquid holder 30 is preferably more than or equal to 0.5 mm and less than or equal to 15 mm.

When the distance Y is more than or equal to 0.5 mm, the penetrations through to the enclosure 30 of protrusions 12 of the microneedle 10 can be of a higher certainty. In addition, contact between the protrusions 12 and the enclosure 32, can be prevented until the user uses the microneedle after being manufactured. Thus, it can be avoided that the enclosure 32 is broken before the microneedle is used and the tip of the protrusions 12 is damaged.

Also, when the distance Y is less than or equal to 15 mm, an increase in the size of the microneedle unit can be prevented. If the size of the microneedle unit increases, there is a possibility that the supporting member 20 will bend or fold, during a period from manufacturing of the microneedle to use of the microneedle unit.

In the microneedle unit according to the present invention, it is also preferred that the distance Y between the tips of the protrusions 12 of the microneedle 10 and the enclosure 32 of the liquid holder 30 is preferably more than or equal to 1 mm and less than or equal to 5 mm.

In the microneedle unit according to the present invention, it is also preferred that, when the area of a region in which each protrusion 12 is formed in the microneedle unit 10 is expressed as S1 and the area of the enclosure 30 is expressed as S2, the area S2 is more than or equal to 1.1 times of the area S1 but less than or equal to 6.0 times of the area S1.

In setting the size of are S2 at 1.1 times greater than or equal to S1, penetration of the protrusions 12 of the microneedle 10 through to the enclosure 32 can be achieved with higher certainty. When the area S2 is set to be less than 6.0 times greater than or equal to the size of S1, the liquid required to be enclosed in the enclosure 30 can be decreased. Also, the penetration of the protrusions 12 of the microneedle 10 through to the enclosure 32 can be achieved with higher certainty.

The area S2 is desirably more than or equal to 1.5 times and less than or equal to 4.0 times bigger than the size S2. In order to suppress the effects of the microneedle 10 in the human body, it is preferable to use bio-compatible material, such as, silicone, metals and resin. More specifically, as the metal, stainless steel, titanium and manganese, for example, can be used. As the resin, for example, a silicone for medical applications, polylactic acid, polyglycolic acid, polycarbonate, or cyclic olefin co-polymer, for example, can be used. However, bio-compatible materials used to form the microneedle 10 in the present invention, is not limited to specific materials.

The microneedle 10 can be formed from materials that are soluble in fluid in the skin or in a liquid held in the liquid holder 30. An example of such a soluble material is a water-soluble macro-molecule. The following can be used such as a water-soluble macromolecule; alginate, curdlan, chitin, chitosan, chitosan succinamide, glucomannan, polymaleic acid, collagen, collagen peptide, hydroxypropyl cellulose, hydroxypropyl methyl cellulose, gelatin or pullulan, for example. The water-soluble macromolecules to form the microneedle 10 in the present disclosure, are however, not limited to specific materials.

The microneedle 10 can be formed from polysaccharide materials, which act as a water-soluble materials with biocompatible characteristics which are soluble in the fluid in the skin, or in the liquid held in the liquid holder 30. Various materials can be used as the polysaccharide, such as dextran, dextrin, trehalose, and maltose can be used, however these poly saccharides are not limited to such materials. When the microneedle 10 is formed from water-soluble materials, the microneedle 10 can contain a drug.

The microneedle 10 can be manufactured using various kinds of conventional techniques. For example, when resin is used as the material for the microneedle 10, various techniques including injection molding, extrusion molding, imprint, hot embossing or casting molding technique for example can be used, to form the microneedle 10. Alternatively, the microneedle 10 can also be formed using a machinery method such as a cutting method or using an etching method.

Still alternatively, the microneedle 10 which has been produced can be used as the original plate to produce a casting mold by a plating method or a molding method which uses resin. The produced casing mold can then be used to reproduce a microneedle 10.

The supporting member 20 is made of a flexible material. As such a flexible material, various kinds of resins can be used, which include, polyethylene, polypropylene, or polyethylene terephthalate. In order to improve the stability of the supporting member 20 accommodating the microneedle, an aluminum laminate or an aluminum deposition film can be applied inside the supporting member 20.

The base material 31 of the liquid holder 30 is made of a material which can be pierced by the protrusions 12. The base material 31, may be made of, for example, a film made of resin, such as polyethylene terephthalate. The liquid can be enclosed into the enclosure 32 by using, for example a packaging technique which is used when liquid such as seasoning or the like is soft-packaged. Liquid contained in a porous body which is, for example, gel materials and sponge, may be enclosed in the enclosure 32. A structure which makes the liquid holder 30 hold a substance to be administered is not limited to packaging which uses a packing member. Any structure is available provided that the liquid containing a substance to be administered can be maintained. By way of example, the liquid holder 30 may be structured to hold the liquid by fixing the porous body itself or by fixing an administered substance itself which is formed into a gel.

As the drug, pharmacologically active agents and cosmetic compositions maybe used. The type of drug is chosen according to the purpose. If the drug is a liquid solution, only the drug itself maybe enclosed in the enclosure 32, or a drug solubilized in an appropriate agent may also be enclosed in the enclosure 32.

As a pharmacologically active agent, various agents such as vaccine for influenza, pain relievers for cancer patients, biological formulas, genetic therapeutic medicine, injection agents, oral agents, or dermatologically applicable agents may be used. In transepidermal administration using a microneedle, a drug is administered through the pores in the skin tissue. For that reason, the transepidermal administration using a microneedle can be applied to the administration of pharmacologically active agents where an injection into a skin tissue is necessary, as well as the conventional method of transepidermal administration of pharmacologically active agents. Particularly for the transepidermal administration using the microneedle, there is no pain when administering, so that this technique is suitable to administer an injection of vaccine to infants, for example. Additionally, as it is not necessary to take the medicine orally at the time of administration, a transepidermal administration using the microneedle is suitable for infants have difficulty taking a drug orally. Therefore the microneedle is suitable for such a drug taken orally.

As a cosmetic composition, cosmetics or beauty products can be used. As the cosmetic composition, for example, moisturizing agents, pigments, fragrances or bioactive agents having beauty effects; effective for wrinkle or acne treatment, or effectively improve stretch marks, or effectively improve hair removal as another example.

The microneedle unit is formed in such a manner that the microneedle 10 fixed to the supporting member 20 and the liquid holder 30 is fixed to the supporting member 20 to which the microneedle 10 fixed. Conventional techniques, such as adhesion using adhesive agents, heat adhesion (heat sealing) or mechanical fitting is used for fixing between the supporting member 20 and the microneedle 10, and for fixing between the supporting member 20 and liquid holder 30.

Figure 3:
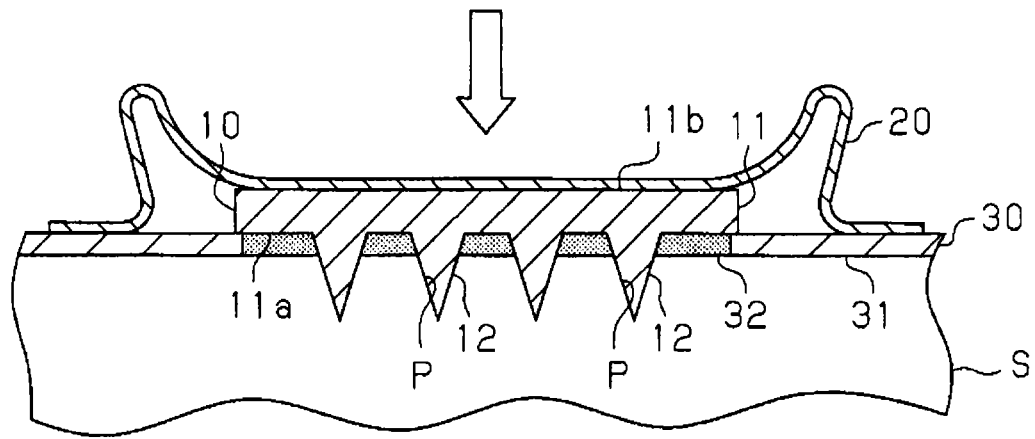
FIG. 3 is a cross sectional view schematically showing the use of the microneedle unit shown in FIG. 1.

The operation of the microneedle unit is described below, with reference to FIG. 3. When the microneedle unit is used, a side of the liquid holder 30 that does not face the microneedle 10 is placed on a skin S. Thus, the tips of the protrusions 12 of the microneedle 10 are opposed to the surface of the skin S through the enclosure 32.

Next, the bottom of the supporting member 20 is pressed from the outer side of the supporting member 20 towards the skin S. Thus, the pressing force is transmitted to the base body 11 through the bottom of the supporting member 20. As a result, as shown in FIG. 3, the protrusions 12 of the microneedle 10 break through the base material 31, which provides the enclosure 32 of the liquid holder 30 and passes through the enclosure 30 to pierce the skin. Perforations P are thus formed in the skin tissue.

The liquid held inside the enclosure 32 passes out of the enclosure 32 through the perforation formed on the base body 31, in response to the breaking through of the protrusion 12. The liquid running out of the enclosure 32 enters the formed perforation P, flowing on the protrusions 12. In addition, after the microneedle unit is removed from the surface of the skin tissue S, the liquid running out of the enclosure 32 and spreading on the surface of the skin tissue S also enters inside the formed perforation P. Thus, the drug is supplied inside the body.

In this way, in the microneedle unit according to this embodiment, the enclosure 32 of the liquid holder 30 is arranged at a position opposed to the tip of the protrusions 12 of the microneedle 10. The protrusions 12 are thus made to penetrate through the enclosure 32 and to pierce the skin tissue. The microneedle 10 and the drug to be administered are combined in advance, so that it is not necessary to confirm the compatibility between the microneedle and the drug at the time of drug administration. Therefore, the usage of an erroneously combined microneedle and drug can be avoided. In addition, the microneedle 10 and liquid holder 30 are held apart from each other until administration of the drug. This separation makes it possible to avoid contact between the microneedle 10 and the drug until just before usage, and thus avoids the deterioration of the microneedle 10 and/or the drug.

In conventional cases in which a drug is applied after removing the microneedle from the skin, the perforations formed by the microneedle may close up in a period from removal of the microneedle to application of the drug. If this occurs, it is difficult for the drug to penetrate inside the skin tissue. In contrast, for the microneedle according to this embodiment, it is easier for the drug to penetrate inside the skin tissue, because the time from the formation of the perforation in the skin tissue to the application of the drug is short.

Mover, the protrusions 12 of the microneedle 10 has two functions, that is, a function of breaking the liquid holder 30, and a function of forming the perforation in the skin tissue. Thus, the configuration of the microneedle unit is simple compared to a configuration where these functions are achieved through different member.

In addition, the solubility of the microneedle 10 can be enhanced if the microneedle 10 is made of a material that is soluble in the solution held in the liquid holder 30, compared to the microneedle 10 soluble in only fluid found in the skin. In a case where a drug is contained within the microneedle 10, the drug contained within the microneedle 10 as well as the drug held in the liquid holder 30 are also allowed to enter perforations P. In this case, a larger amount of drugs can thus be supplied inside the body.

Figure 4:
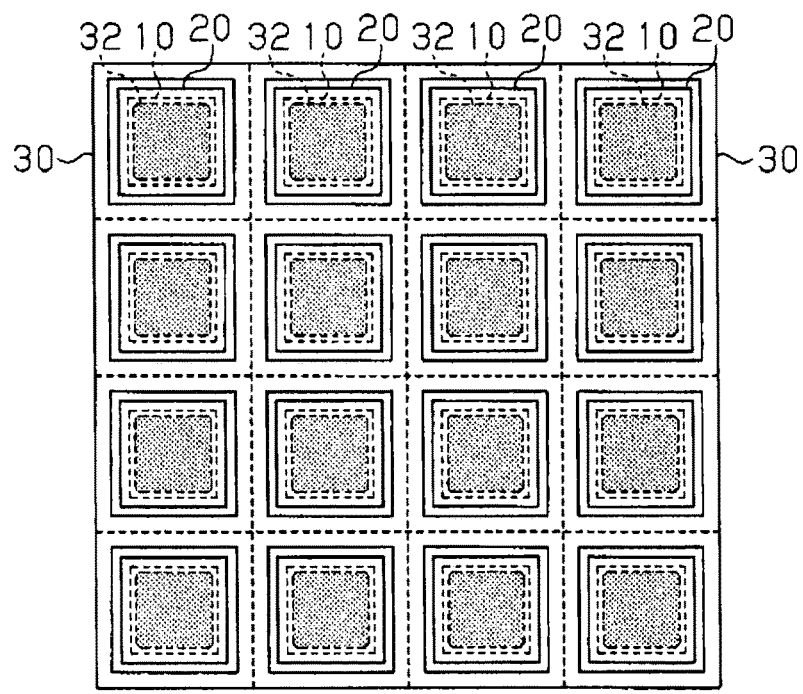
FIG. 4 is a planar view showing microneedle units connected to each other in the first embodiment.

The microneedle may be provided as a single microneedle or a plurality of microneedles joined together to each other accordingly, as described below. As shown in FIG. 4, a plurality of microneedles may be provided in a matrix form joined to each other to provide a single sheet configuration.

Figure 5:
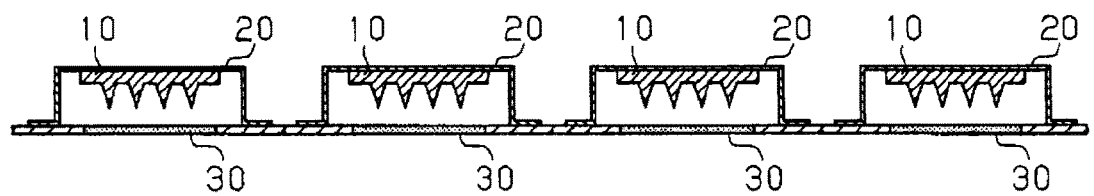
FIG. 5 is a cross sectional view showing microneedle units connected to each other in the first embodiment.

As shown in FIG. 5, the end of the liquid holder 30 of each of the microneedle units is joined to the end of another adjacently-located microneedle unit. In this configuration, when perforations are formed at the joined part of the liquid holders 30, the microneedle units can be separated easily. In cases where, as shown in the figure, a plural of microneedle units are joined to each other, a large number of microneedle units can be manufactured with higher efficiency.

EXAMPLES

The functions of the microneedle units, described above, will now be described using the following specific examples.

Example 1

Production of the Microneedle

First, an original microneedle made of a silicon-made substrate was produced using precision machining. The formation of the protrusion was a square prism (height: 400 μm, bottom face 50 μm×150 μm), on top of the base body, 36 protrusions were arranged in a lattice of 6 rows of 6 columns with a 1 mm interval therebetween. The size of the region wherein the protrusions were formed was 35 mm$^2$.

Subsequently, a nickel membrane with a 500 μm thickness was formed on the original microneedle, using the plating method. Thereafter, using a 30% weight vol/vol potassium hydroxide solution heated to 90° C., the original microneedle made of silicon was removed using a wet etching technique and thus a nickel mold was made.

Thereafter, the molding material polycarbonate, which is a forming material was place on the produced mold, and a polycarbonate microneedle was reproduced using the heat imprint method.

<Production of the Supporting Member>

The polyethylene terephthalate (PET) film was processed into a square column recess with a flat part on the rim of the recess, as shown in FIG. 1, whereby a supporting member was produced.

<Production of the Liquid Holder>

Two layers of the PET film were overlapped one on the other, one of the ends was sealed with a hot melt, and the liquid containing a drug was filled therein. Thereafter the other end of the 2 layered PET film was closed using the hot melt, thus producing the liquid holder. A water solution of 0.1% rhodamine was used as the liquid containing the drug. The size of the enclosure of the liquid holder was 64 mm$^2$.

<Production of the Microneedle Unit>

The base body of the microneedle was attached to an internal side of the supporting member using an adhesion agent. Subsequently, the supporting member and the liquid holder was adhered to each other adhesion agent, such that the microneedle attached to the supporting member is positioned in the center of the liquid holder. There was a 1.5 mm distance between the tips of the protrusions of the microneedle and the enclosure of the liquid holder.

Thus, the microneedle unit in the example 1 was obtained.

<Validation Testing>

After a perforations were pierced in the skin of a pig by pressing the microneedle unit according to the example 1, the skin of the pig was observed using a confocal microscope.

The results from the validation confirmed that rhodamine fluorescence occurred in the dermis of the pig skin tissue. These results suggested that in pressing the microneedle unit, the protrusions broke through the liquid holder and the rhodamine that flowed therethrough was absorbed in the pig skin tissue.

The maximum protruding length L of the respective protrusions of the microneedle unit described in example 1 was 200 µm.

Example 2

Production of the Microneedle Unit

First, an original microneedle made of silicon was produced using precision machining. The formation of each of the protrusions was a square prism (height: 400 µm, bottom face 150 µm×150 µm) and on top of the base body there were 36 protrusions are arranged in a lattice of 6 rows of and 6 columns with an 1 mm interval therebetween.

Subsequently, a nickel membrane with a thickness of 500 µm was formed on the original microneedle, using the plating method. Thereafter, using a 30% weight vol/vol of potassium hydroxide solution heated to 90° C., the original microneedle made of silicon was removed using a wet etching technique and thus the nickel mold was formed.

The produced mold was then filled with chitosan succinamide solution by the injection method, dried and fixed, and thus a chitosan succinamide microneedle was reproduced.

<Production of the Supporting Member>

As shown in FIG. 1, a polyethylene terephthalate (PET) film was processed into a formation where there was a square column formation with a recess, and a flat formation on the rim of the recess part, using the vacuum compression forming method, thus the supporting member was produced.

<Production of the Liquid Holder>

The liquid holder was produced by overlaying two layers of the PET film one on the other, sealing one of the ends with a hot melt technique and filling the joined PET films with a liquid containing the drug. Thereafter the other end of the 2 layered PET film was then closed using the hot melt, to produce the liquid holder. A 0.1% rhodamine solution was used as the drug containing solution.

<Production of the Microneedle Unit>

The base body of the microneedle was attached to a side of the inner part of the supporting member using an adhesion agent. Subsequently, the supporting member and the liquid holder were adhered to each other using an adhesion agent, such that the microneedle attached to the supporting member is positioned in the center of the liquid holder. As a result, the microneedle unit in the example 2 was obtained <Validation Testing>

After perforations were pierced in the skin of a pig by pressing the microneedle unit in example 2, the skin of the pig was observed using a confocal microscope.

The results from the validation confirmed that rhodamine fluorescence was inside the dermal of the skin tissue of the pig. These results suggested that in pressing the microneedle unit, according to example 2, the protrusions broke through the liquid holder and the rhodamine that flowed therethrough was absorbed in the skin of the pig.

The maximum protruding length L of each of the protrusions for the microneedle unit described in example 2 was 200 µm. When the protrusions of the microneedle of the microneedle unit was observed under the microscope, it was confirmed that the tip of the protrusion had disappeared in a microscope image after piercing the pig skin. This suggested that the microneedle produced from chitosan succinamide was solubilized in the rhodamine solution.

In the above examples 1 and 2, both the microneedle units, one of which has the microneedle which does not dissolve in the drug and the other of which has the microneedle which dissolves in the drug, showed that the drug can be appropriately administered into the skin tissue.

As described above, according to this embodiment the following merits can be achieved.

(1) Since the microneedle 10 and the drug to be administered are previously combined with each other, it is not necessary to confirm compatibility between the drug and the microneedle 10 at the time of administration. Additionally, until a time immediately before actual administration of a substance to be administered, the microneedle 10 and the liquid holder are kept to be opposed to each other without contact therebetween. Hence, it is possible to avoid contact between the microneedle unit 10 and the drug, resulting in that deterioration, i.e., changing in quality, of the microneedle unit 10 and/or the drug is avoided or reduced.

(2) It is also possible to avoid the perforations, formed by the microneedle, from being closed before a substance is administered, thus the substance easily penetrates into the skin tissue.

(3) In the liquid holder 30, the liquid containing the drug is enclosed around the base material. Thus, since scattering the liquid in the microneedle unit can be avoided, contact between the scattered liquid and the microneedle 10 is also avoided. As a result, an effect for superseding deterioration of the microneedle 10 can be enhanced.

(4) The supporting member 20 is used as a container accommodating the microneedle 10 therein. Since the opening of the supporting member 20 is closed by the liquid holder 30, the tips of the protrusions 12 of the microneedle 10 supported by the supporting member 20 are arranged in a position opposed to the enclosure 32 of the liquid holder 30. Accordingly, this simple configuration makes it possible to provide the microneedle unit with the foregoing merits (1) and (2). Furthermore, the microneedle 10 can be protected from the exterior through the supporting member 20 and the liquid holder 30. Thus, there is no need to provide a separate member to protect the microneedle 10.

(5) The tip of the protrusions 12 can penetrate through the enclosure 32 by pressing the bottom of the supporting member 20. The microneedle 10 can therefore be displaced through this simple pressing configuration. Since the tip of the protrusion 12 is displaced by the structural deformation of the supporting member 20 itself, it is easier to check, from outside the container, whether or not the tip of the protrusion 12 and the liquid holder 30 have been in mutual contact, even if the microneedle 10 is configured such that the microneedle is accommodated inside the container. Additionally, the microneedle 10 can easily pierce the skin tissue of any part of the body, compared to a formation in which the liquid holder 30 is pressed towards the microneedle 10.

(6) Because the protrusions 12 are made of a material that is soluble in a solution held in the liquid holder 30, the solubility of the protrusion 12 in the skin can be enhanced, compared to the protrusions 12 soluble which are the fluid of the skin only.

The embodiments described above can be modified as will be described below.

A perforation may be formed in each of the protrusions 12. The perforations may be a perforation penetrating through the tip of the protrusion part 12 to the bottom face of the base body 11, or a perforation that does not penetrate therethrough. There may be a groove formed on the tip or the surrounding of the protrusions 12. The perforation and/or the groove of the protrusion 12 can be formed in a position such that the liquid inside the enclosure 32 enters therethrough when the protrusion 12 is passing through the enclosure 32 of the liquid holder 30. In this configuration, the liquid that entered into the perforation and/or the groove of the protrusions 12 can enter the skin tissue and be carried inside each preformation formed by the microneedle in the skin tissue. Thus, as the liquid leaking from the perforation formed in the skin tissue by the microneedle can be prevented, the drug contained in the liquid can also be appropriately supplied into the skin tissue.

The base body 11 and the protrusion 12 maybe made of materials that are different from each other. The protrusions 12 only may be formed from a material that is soluble in the liquid held in the liquid holder 30, for example. As long as the protrusions part 12 are made of a material that is soluble in the liquid held in the liquid holder 30, the above described merit (6) can be obtained.

The microneedle 10 and the supporting member 20 may be configured as a single unit depending on the materials of the microneedle 10 and the supporting member 20. Alternatively, it is also possible to employ a configuration where a side wall of the supporting member 20 may also serve as the base body 11 of the microneedle 10.

The supporting member 20 may be a container which does not cover the microneedle 10. The supporting member 20 may be configured to support the microneedle 10 at its portion different from the fixed face 11b of the base body 11 of the microneedle 10. By way of example, the supporting member 20 may be configured to support the four corners of the base body 11 of the microneedle 10, so that this is also able to support the microneedle 10. In short, it is sufficient that the supporting member 20 supports the microneedle 10 in a displaceable manner at its position where the tips of the productions 12 of the microneedle 10 and the enclosure 32 of the liquid holder 30 are opposed to each other. Another modification is concerned with the base body 11, where the base body 11 is shaped to be supported by the supporting member 20 such that the tips of the protrusions 12 can be displaced to their positions where the tips of the productions 12 pass through the liquid holder 30.

The microneedle 10 may be configured such that The microneedle 10 is made to be displaced from its position where the tips of the protrusions 12 are opposed to the enclosure 32 to its position where the tips of the protrusions 12 penetrate through the enclosure 32, by using methods other than the foregoing method of pressing the bottom of the supporting member 20. For example, a through-hole may be formed through the bottom of the supporting member 20, so that an instrument can be used to be passed through the through-hole. Hence, the instrument is able to directly press the microneedle 10, thus making it possible to displace the microneedle 10. This alternative configuration may still be modified into another configuration where pressing the instrument to the microneedle allows the microneedle 10 to be released from the supporting member 20. In this modification, the supporting member 20 may be provided as a rigid member with no flexibility.

The configuration for enabling the supporting member 20 to support the microneedle 10 in a displaceable manner, is not limited to a configuration in which the supporting member 20 itself is modified in its structure. For example, the supporting member 20 can be a mechanical latch system which is able to displace the microneedle 10 towards the liquid holder 30 responsively to an external force applied to the supporting member 20.

One technical problem was that the depth and the size of the perforations needed to allow the drug to be absorbed into a body differ depending on each type of drug. The microneedle is therefore made to a different formation for each type of drug, in order to form the various perforation types. On the other hand, for the drug administration method described above, a microneedle forming the perforations and a drug applied after the perforations are formed, are usually managed separately from each other. Hence, the user is obliged to confirm the compatibility of the microneedle type and the drug each time the drug is administered. Thus, the preparation work required when the drug is administered unavoidably becomes complex.

Meanwhile, recently, a microneedle that is pre-treated with a drug on the surface of the protrusions has been developed. This type of microneedle may however cause the microneedle and the drug to react with each other, in which either one or both of the microneedle and drug deteriorate. Hence, when the microneedle is pre-treated with a drug on the surface of the protrusions, there is a limitation to the number of possible combinations between a microneedle material and a drug, which is adaptable to such microneedles.

It is thus desired to develop the technique of administrating drugs using a microneedle, in which the contact between the microneedle and the drug to be administered can be avoided and compatibility between the microneedle type and the drug can be confirmed easily.

The object of the presently disclosed technique is to avoid contact between the substance to be administered and the microneedle and to provide a microneedle unit which is able to decrease work load in confirming compatibility of the microneedle type and the drug to be administered One aspect of the disclosed microneedle unit includes a liquid holder, a microneedle, and a supporting member. The liquid holder is provided with a part holding liquid containing a substance to be administered. The microneedle is provided with a base body and a protrusion extending from a surface of the base body, the protrusion having a hardness which enables the protrusion to penetrate through the liquid holder. The supporting member supports the base body such that i) the microneedle is arranged at a position where a tip of the protrusion and the part holding the liquid are opposed to each other with a gap provided therebetween and ii) the tip of the protrusion is allowed to be displaced to a position where the tip of the protrusion penetrates through the liquid holder in response to an external force applied to the base body.

According to the aspect described above, the microneedle is supported in the state where the tip of the protrusion and the liquid holder are apart from each other, and when the base body receives an external force, the tip of the protrusion penetrates through the liquid holder. Since the microneedle and the substance to be administered are pre-determined for compatibility, it is not necessary to confirm the compatibility of the microneedle type and the substance to be administered when administering the substance. Furthermore, as the microneedle and the liquid holder are apart from each other until immediately before administering the substance, contact between the microneedle and the substance to be administered is avoided for a long period. As a result, a change in quality of the microneedle and substance to be administered is also avoided. Furthermore, as a consequence, the contact between the microneedle and the substance to be administered is avoided, and the work load of confirming the compatibility of the microneedle and the substance to be administered is decreased.

It is preferred that, in the microneedle unit, the liquid holder is a packing member in which the liquid is contained.

According to the above configuration, the liquid can be suppressed from scattering in the microneedle unit, so that contact between the scatted liquid and the microneedle can also be avoided. Additionally, the effect of suppressing a change in quality of the microneedles can be enhanced.

It is preferred that the supporting member is a concave shaped container provided with an opening, the liquid holder is configured to close the opening, and the microneedle is accommodated inside the container.

According to the configuration described above, the microneedle unit is accommodated in a space sectioned by the supporting member and liquid holder. Thus, the microneedle is protected from the exterior by the supporting member and the liquid holder.

It is also preferred that, in the foregoing microneedle unit, the body base is formed into a plate shape provided with the surface having the protrusion and a rear surface fixed to a bottom of the container; and the bottom of the container is flexible such that the bottom receives a pressing force directed towards the opening of the container and bends towards the opening, whereby the base body receives the external force.

According to the configuration described above, since the tip of the protrusion is displaced through the transformation of the supporting member itself, even if the microneedle is configured to be accommodated inside the container, it is easy to recognize whether the tip of the protrusion and the liquid holder have been in contact to each other, from the exterior of container.

It is also preferred that, in the microneedle unit described above, the protrusion is made of a material soluble in the liquid held in the liquid holder.

In this configuration, compared to a protrusion that is soluble only in the fluids in the skin, solubility of the protrusion inside the skin can be enhanced.

According to the presently disclosed technique, contact of a substance to be administered and a microneedle can be avoided before administration, and a work load of confirming the compatibility of a microneedle and a substance to be administered can be decreased.

REFERENCE SIGNS LIST

10 . . . Microneedle,
11 . . . base body,
12 . . . protrusion,
20 . . . supporting member,
30 . . . liquid holder,
31 . . . base material,
32 . . . enclosure.

Obviously, numerous modifications and variations of the present invention are possible in light of the above teachings. It is therefore to be understood that within the scope of the appended claims, the invention may be practiced otherwise than as specifically described herein.

What is claimed is:

1. A microneedle unit, comprising:
a liquid holder comprising a base material and having an enclosure portion surrounded by the base material such that the enclosure portion holds and seals a liquid in the base material;
a microneedle having a base body and a protrusion extending from a surface of the base body such that the protrusion has a hardness that allows the protrusion to penetrate through the enclosure portion of the liquid holder; and
a container having a concaved shape and supporting the microneedle inside the container such that the microneedle is positioned at a bottom of the container and that a tip portion of the protrusion and the enclosure portion holding the liquid are opposed to each other with a gap therebetween,
wherein the liquid includes a substance to be administered, and the liquid holder is adhered to the container to close an opening of the container at an end of the container on an opposite side with respect to the bottom of the container such that the microneedle is accommodated inside the container, that the tip portion of the protrusion of the microneedle faces the enclosure portion of the liquid holder and that the container moves the tip portion of the protrusion of the microneedle toward the enclosure portion of the liquid holder and the tip portion penetrates through the enclosure portion of the liquid holder when an external force is applied to the bottom of the container.

2. The microneedle unit according to claim 1, wherein the base material of the liquid holder comprise polyethylene terephthalate.

3. The microneedle unit according to claim 2, wherein the liquid holder is adhered to the container to close the opening of the container at the end of the container on the opposite side with respect to the bottom of the container such that the enclosure portion of the liquid holder has an area in a size of 1.1 times greater than or equal to a size of an area in which the protrusion is formed.

4. The microneedle unit according to claim 3, wherein the base body has a plate shape having a rear surface fixed to the bottom of the container, and the container is flexible such that when the bottom receives a pressing force directed towards the opening of the container, the container bends towards the opening.

5. The microneedle according to claim 2, wherein the protrusion is made of a material soluble in the liquid held in the liquid holder.

6. The microneedle according to claim 2, wherein the protrusion is formed in a plurality on the surface of the base body, the plurality of protrusions are positioned such that the plurality of protrusions faces the enclosure portion of the liquid holder, and the enclosure portion has an area larger than an area on the surface of the base body where the protrusions are formed.

7. The microneedle unit according to claim 1, wherein the liquid holder is adhered to the container to close the opening of the container at the end of the container on the opposite side with respect to the bottom of the container such that the enclosure portion of the liquid holder has an area in a size of 1.1 times greater than or equal to a size of an area in which the protrusion is formed.

8. The microneedle unit according to claim 7, wherein the base body has a plate shape having a rear surface fixed to the bottom of the container, and the container is flexible such that when the bottom receives a pressing force directed towards the opening of the container, the container bends towards the opening.

9. The microneedle according to claim 8, wherein the protrusion is made of a material soluble in the liquid held in the liquid holder.

10. The microneedle according to claim 8, wherein the protrusion is formed in a plurality on the surface of the base body, the plurality of protrusions are positioned such that the plurality of protrusions faces the enclosure portion of the liquid holder, and the area of the enclosure portion is larger than an area on the surface of the base body where the protrusions are formed.

11. The microneedle according to claim 7, wherein the protrusion is made of a material soluble in the liquid held in the liquid holder.

12. The microneedle according to claim 7, wherein the protrusion is formed in a plurality on the surface of the base body, the plurality of protrusions are positioned such that the plurality of protrusions faces the enclosure portion of the liquid holder, and the area of the enclosure portion is larger than an area on the surface of the base body where the protrusions are formed.

13. The microneedle according to claim 7, wherein the liquid holder is a film having the liquid sealed in the enclosure portion of the film.

14. The microneedle according to claim 1, wherein the protrusion is made of a material soluble in the liquid held in the liquid holder.

15. The microneedle according to claim 1, wherein the protrusion is formed in a plurality on the surface of the base body, the plurality of protrusions are positioned such that the plurality of protrusions faces the enclosure portion of the liquid holder, and the enclosure portion has an area larger than an area on the surface of the base body where the protrusions are formed.

16. The microneedle according to claim 1, wherein the liquid holder is adhered to the container to close the opening of the container at the end of the container on the opposite side with respect to the bottom of the container such that the enclosure portion of the liquid holder has an area in a size of 1.5 times greater than or equal to a size of an area in which the protrusion is formed and less than or equal to 4.0 times the size of the area in which the protrusion is formed.

17. The microneedle unit according to claim 16, wherein the base body has a plate shape having a rear surface fixed to the bottom of the container, and the container is flexible such that when the bottom receives a pressing force directed towards the opening of the container, the container bends towards the opening.

18. The microneedle according to claim 16, wherein the protrusion is made of a material soluble in the liquid held in the liquid holder.

19. The microneedle according to claim 16, wherein the protrusion is formed in a plurality on the surface of the base body, the plurality of protrusions are positioned such that the plurality of protrusions faces the enclosure portion of the liquid holder, and the area of the enclosure portion is larger than an area on the surface of the base body where the protrusions are formed.

20. The microneedle according to claim 1, wherein the liquid holder is a film having the liquid sealed in the enclosure portion of the film.

* * * * *